US009789064B2

(12) United States Patent
Parente Dueña et al.

(10) Patent No.: US 9,789,064 B2
(45) Date of Patent: Oct. 17, 2017

(54) METHOD FOR DELIVERING A PEPTIDE TO A SUBJECT AT A MODULATED RATE VIA MICROCAPSULES OF LACTIC-CO-GLYCOLIC COPOLYMER CONTAINING SAID PEPTIDE

(75) Inventors: Antonio Parente Dueña, Barcelona (ES); Josep Garcés Garcés, Barcelona (ES); Angel Bonilla Muñoz, Barcelona (ES); David Cunillera Colomé, Barcelona (ES)

(73) Assignee: GP PHARM, S.A., Barcelona (ES)

(*) Notice: Subject to any disclaimer, the term of this patent is extended or adjusted under 35 U.S.C. 154(b) by 0 days.

(21) Appl. No.: 12/148,893

(22) Filed: Apr. 23, 2008

(65) Prior Publication Data

US 2008/0233198 A1 Sep. 25, 2008

Related U.S. Application Data

(62) Division of application No. 11/042,682, filed on Jan. 25, 2005, now abandoned, which is a division of application No. 09/913,671, filed as application No. PCT/ES00/00475 on Dec. 15, 2000, now abandoned.

(30) Foreign Application Priority Data

Dec. 17, 1999 (ES) ...................... 9902768

(51) Int. Cl.
*A61K 9/50* (2006.01)
*A61K 38/09* (2006.01)
*A61K 9/16* (2006.01)

(52) U.S. Cl.
CPC .......... *A61K 9/1647* (2013.01); *A61K 9/1617* (2013.01); *A61K 9/5015* (2013.01); *A61K 9/5031* (2013.01)

(58) Field of Classification Search
None
See application file for complete search history.

(56) References Cited

U.S. PATENT DOCUMENTS

| | | | |
|---|---|---|---|
| 2,151,185 A | 3/1939 | Carruthers et al. | |
| 3,773,919 A | 11/1973 | Boswell et al. | |
| 4,652,441 A | 3/1987 | Okada et al. | |
| 4,728,721 A | 3/1988 | Yamamoto et al. | |
| 4,917,893 A | 4/1990 | Okada et al. | |
| 4,954,298 A | 9/1990 | Yamamoto et al. | 264/4.6 |
| 5,330,767 A | 7/1994 | Yamamoto et al. | |
| 5,445,832 A | 8/1995 | Orsolini et al. | |
| 5,518,730 A | 5/1996 | Fuisz | 424/426 |
| 5,525,646 A | 6/1996 | Mathisen et al. | |
| 5,536,508 A | 7/1996 | Canal et al. | 424/501 |
| 5,538,739 A | 7/1996 | Bodmer et al. | 424/501 |
| 6,818,018 B1 * | 11/2004 | Sawhney | 623/11.11 |

FOREIGN PATENT DOCUMENTS

| | | |
|---|---|---|
| CH | 661206 A5 | 7/1987 |
| CH | 665558 A5 | 5/1988 |
| DE | 19545257 | 6/1997 |
| EP | 0145240 | 4/1989 |
| EP | 0190833 B1 | 3/1991 |
| EP | 0202065 B1 | 4/1993 |
| EP | 0052610 B2 | 10/1994 |
| ES | 2009346 | 9/1989 |
| ES | 2020890 | 10/1991 |
| ES | 2037621 | 6/1993 |
| GB | 2209937 | 6/1989 |
| WO | WO 94/21237 | 9/1994 |
| WO | 97/14408 | 4/1997 |
| WO | WO 97/14408 | 4/1997 |
| WO | WO 97/12549 | 3/1999 |

OTHER PUBLICATIONS

C. Pitt et al., "Sustained Drug Delivery Systems. I. The Permeability of Poly($\epsilon$-Caprolactone), Poly(DL-Lactic Acid), and Their Copolymers", *Journal of Biomedical Materials Research*, 13:497-507 (1979).
Pitt et al., "Sustained Drug Delivery Systems. I. The Permeability of Poly($\epsilon$-Caprolactone), Poly(DL-Lactic Acid), and Their Copolymers"; *Journal of Biomedical Materials Research*, vol. 13, 1979, pp. 497-507.
Cumillera et al., "Leuprolide Microcapsules GP-Pharm Depot 7.5 mg: In Vivo Trials," Abstract 249, Programme for the European Conference on Drug Delivery and Pharmaceutical Technology, p. 149, Sevilla-Spain, May 10-12, 2004.
Cumillera et al., "Leuprolide Microcapsules GP-Pharm Depot 7.5 mg: In Vivo Trials," Poster, European Conference on Drug Delivery and Pharmaceutical Technology, Sevilla-Spain, May 10-12, 2004.
Herranz et al., "Evaluation of the Testosterone Suppressive Effect of Leuprolide Acetate 3.75 and 7.5 mg Depot, GP-Pharm SA, vs. Market References in a Pilot Clinical Trial With Healthy Male Volunteers," Poster, European Conference on Drug Delivery and Pharmaceutical Technology, Sevilla-Spain, May 10-12, 2004.
GP-Pharm, S.A., Leuproreline Acetate GP-Pharm 3.75 mg Depot, Batch No. 00405-1, Analitical Bulletin, Jun. 11, 2010, 1 page.
Leitner et al., "The Pharmacokinetics and Pharmacodynamics of a New Sustained-Release Leuprolide Acetate Depot Compared to Market Refefernces," International Journal of Clinical Pharmacology and Therapeutics, vol. 46, No. 8/2008, pp. 407-414 (Exhibit K).
Exhibit J—Percentages of triethyl citrate in Examples, determined by analysis of the microcapsules, 1 page.
Exhibit I—The detailed analytical procedure for the determination of the TEC content in the microcapsules, 4 pages.
Exhibit L—Summary of Product Characteristics Lutrate® Depot 3.75 mg, available on-line as of Nov. 19, 2012, using the Human Medicines Agencies Index and found, e.g., at the following URL http://mri.medagencies.org/Human/Product/Details/20665, 18 pages.

(Continued)

*Primary Examiner* — Jessica Worsham
(74) *Attorney, Agent, or Firm* — Kenneth H. Sonnenfeld; Bryte V. Kelly; King & Spalding LLP

(57) ABSTRACT

Micro-capsules for the slow release of drugs, consisting of a lactic-co-glycolic copolymer to which a plasticizer has been incorporated and which contain a drug of pharmaceutical interested within them.

10 Claims, 1 Drawing Sheet

(56) References Cited

OTHER PUBLICATIONS

Exhibit M—Summary sent by facsimile to Examiner prior to Examiner interview of Nov. 19, 2013, 5 pages.
Gombotz, W. et al., Biodegradable Polymers for Protein and Peptide Drug Delivery, Bioconjugate Chem., 1995, 6, 332-351.
Yolles, S. et al., Controlled Release of Biologically Active Drugs, Bulletin of the Parenteral Drug Association, Nov.-Dec., 1976, vol. 30, No. 6, 306-312.
Sanders, L. et al., Controlled Delivery of Nafarelin, An Agonistic Analogue of LHRH, From Microspheres of Poly (D,L Lactic-co-glycolic) Acid, Delivery Systems for Peptide Drugs, NATO ASI p. 125-136, Syntec Research, Palo Alto, CA.
Sansdrap, P. et al., Influence of additives on the release profile of nifedipine from poly(DL-lactide-co-glycolide) microspheres, J. Microencapsulation, 1998, vol. 15, No. 5, 545-553.
Urata et al., "Modification of release rates of cyclosporin A from polyl(L-lactic acid) microspheres by fatty acid esters and in-vivo evaluation of the microspheres," Journal of Controlled Release 58, pp. 133-141, 1999.
Wang et al., "Preparation and Characterization of Poly(lactic-co-glycolic acid) Microspheres for Targeted Delivery of a Novel Anticancer Agent, Taxol," Chem. Pharm. Bull., 44(10), pp. 1935-1940, 1996.

* cited by examiner

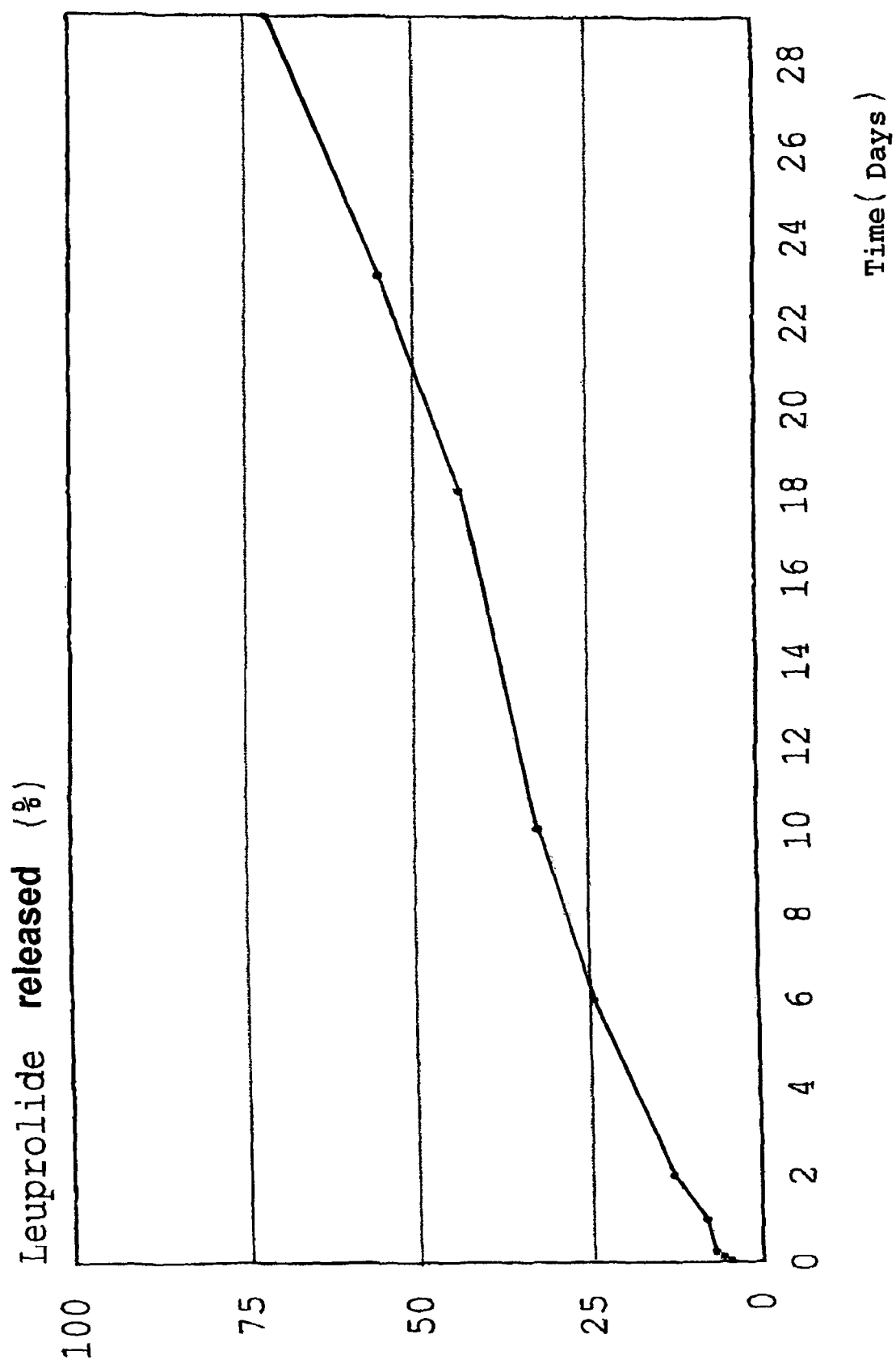

METHOD FOR DELIVERING A PEPTIDE TO A SUBJECT AT A MODULATED RATE VIA MICROCAPSULES OF LACTIC-CO-GLYCOLIC COPOLYMER CONTAINING SAID PEPTIDE

CROSS REFERENCE TO RELATED APPLICATIONS

The present application is a divisional of U.S. patent application Ser. No. 11/042,682, filed Jan. 25, 2005, which is in turn a divisional of U.S. patent application Ser. No. 09/913,671, filed Sep. 24, 2001, which is a 35 U.S.C. §371 national phase conversion of PCT/ES00/00475, filed Dec. 15, 2000, which claims priority of Spanish Patent Application No. 9902768, filed Dec. 17, 1999.

The present invention relates to a new type of micro-capsule or micro-bead for the sustained administration of drugs and to a procedure for their preparation.

A large variety of administration systems have been proposed for drugs that require administration over a long time period. The strategy described in the literature as the most successful is that of micro-encapsulation of the drug to administer in a polymer material of the biodegradable and biocompatible polyester type, such as polylactic-co-glycolic (PLGA). There are a large number of bibliographic references to this strategy, such as: U.S. Pat. No. 5,445,832; ES 2009346; CH 661 206; CH 665 558; ES 2037621; U.S. Pat. No. 4,652,441; ES 2020890; U.S. Pat. No. 4,728,721; U.S. Pat. No. 5,330,767; U.S. Pat. No. 4,917,893; U.S. Pat. No. 4,652,441; EP 0 145 240; EP 0 2020 065; EP 0 190 833, among others for example.

These polymers have the peculiarity that they are degraded slowly within the body releasing the drug contained inside, and the products of this degradation (lactic acid and glycolic acid) are naturally present within the organism.

In the micro-capsules described in the literature of the state of the art it is very hard to achieve a satisfactory modulation of the encapsulated drug release, and to avoid an initial large drug release, as this can only be achieved by changing the composition of the polymer (the ratio of lactic-glycolic acid or the molecular weight thereof), which usually implies making important changes in the procedure for the production of the micro-capsules every time a modification in the drug release profile is desired.

In the article published by Pitt el al. in the Journal of Biomedical Materials Research, Vol. 13, pg 497-507, 1979, it is described that tributyl citrate accelerates the release of drugs, for example, progesterone, in microcapsules of poly-lactic polymers.

As a fruit of our research, we have surprisingly discovered that the addition of small amounts of citric acid esters, to the polymer constituting the micro-capsules, allows a very effective modulation of the liberation characteristics of the micro-capsules obtained, without the need to modify the composition of the polymer.

In the present specification the term modulating release from microcapsules is understood to mean a reduction in the initial release of encapsulated drug and a release of said drug that is almost linear in time. It is both surprising and unexpected, in view of that described by Pitt et al. that the incorporation of small amounts of citric acid ester into the microcapsule preparation of lactic-co-glycolic polymer that encapsulate a peptide of pharmaceutical interest allows the release of the drug to be almost linear and without the presence of sudden initial releases of the drug.

Therefore, the object of this invention consists of providing pharmaceutical preparations of micro-capsules of polymers of lactic and glycolic acid plastified with small quantities of citric acid esters and which contain peptides.

The present invention also comprises the preparation and use of the aforementioned microcapsules.

The citric acid esters useful for the purposes of the present invention are those normally used as plasticizers for pharmaceutical polymers, such as triethyl citrate, tributyl citrate and acetyl tributyl citrate. Use of triethyl citrate is preferable.

By peptides of pharmaceutical interest it is understood:
- analogues of LHRH such as triptorelin, leuprolide, goserelin, buserelin or cetrorelix
- analogues of somatostatin such as somatostatin or octreotide
- analogues of human calcitonin such as salmon calcitonin or carbocalcitonin.

BRIEF DESCRIPTION OF THE DRAWINGS

FIG. 1 shows percent leuprolide drug released by the microcapsules over time (days).

The preparation of the micro-capsules can be carried out following any of the methods described in the literature such as, for example, those described in the U.S. Pat. No. 3,773,919. By way of description and without limitation thereto, the different procedures for producing micro-capsules of the invention would be grouped into the following sections:

a) Method of Coacervation:

A solution of polymer is prepared along with tri-ethyl citrate in a suitable solvent. The drug to be encapsulated is suspended in the polymer and plasticiser solution and a non-solvent of the polymer is added to force deposition of the polymer on the drug crystals. Examples of these procedures without using plasticiser can also be found in documents such as ES 2009346 or EP 052510.

b) Double Emulsion Methods:

The drug to be encapsulated is dissolved in water or in a solution of some other co-adjuvant and is emulsified in a solution of the polymer and the plasticiser in a suitable solvent such as dichloromethane, for example. The resulting emulsion is in turn emulsified in water or in an aqueous solution of an emulsifier such as polyvinylic alcohol. Once this second emulsion has been carried out, the solvent in which the polymer was dissolved is eliminated through evaporation or extraction. The resulting micro-capsules are obtained directly by filtration. Examples of these procedures that do not use the plasticiser can also be found in documents such as U.S. Pat. No. 4,652,441.

c) Simple Emulsion Method:

The drug to be encapsulated, the polymer and the plasticiser are dissolved together in a suitable solvent. This solution is emulsified in water or in a solution of an emulsifier such as polyvinyl acid, and the organic solvent is eliminated by evaporation or extraction. The resulting micro-capsules are recovered by filtration. Examples of these procedures that do not use the plasticiser can also be found in documents such as U.S. Pat. No. 5,445,832.

d) Methods of Solvent Evaporation:

The drug to be encapsulated, the polymer and the plasticiser are dissolved together in a suitable solvent. This solution is evaporated to dryness and the resulting residue reduced down to a suitable size. Examples of this procedure, although not using the plasticiser, can be also be found in documents such as GB 2,209,937.

In the present invention, in all cases, the citric acid ester is deposited along with the polymer, plastifying it and advantageously modifying the hydrophobicity, flexibility and coating capacity characteristics of the polymer and the release profile of the micro-capsules obtained.

This is reducing the initial release of the encapsulated drug and making this release almost linear in time.

The present invention is now described by means of following, non-limiting examples:

EXAMPLE 1: PRODUCTION OF MICRO-CAPSULES, CONTAINING LEUPROLIDE ACETATE, WHICH PRESENTS A DRUG RELEASE PROFILE SUITABLE FOR ONE MONTH 3 g of tri-ethyl citrate and 1.45 g of lactic-co-glycolic polymer (mw=50000 with monomer ratio of 1/1) are dissolved in 50 ml of dichloromethane. When the polymer is fully dissolved 67 mg of leuprolide acetate are added and then suspended by sonication.

63 g of silicone of 350 cts is added slowly with intensive stirring. And when all the silicone has been added the content of the reactor is poured onto 2.5 l of n-heptane and stirred for 1 hour.

The micro-capsules are recovered by filtration and dried under vacuum for 48 hours.

EXAMPLE 2: PRODUCTION OF MICRO-CAPSULES WITH ONE-MONTH RELEASE CONTAINING OCTREOTIDE ACETATE 2 g of tri-ethyl citrate and 1.45 g of lactic-co-glycolic polymer (mw=50000 with monomer ratio of 1/1) are dissolved in 50 ml of dichloromethane. When the polymer is fully dissolved 67 mg of octreotide acetate are added and then suspended by sonication.

70 g of silicone of 350 cts is added slowly with intensive stirring. And when all the silicone has been added the content of the reactor is poured onto 2.5 l of n-heptane and stirred for 1 hour.

The micro-capsules are recovered by filtration and dried under vacuum for 48 hours.

EXAMPLE 3: PRODUCTION OF MICRO-CAPSULES WITH A THREE-MONTH RELEASE PROFILE CONTAINING TRIPTORELINE ACETATE 2 g of tri-ethyl citrate and 1.45 g of lactic-co-glycolic polymer (mw=50000 with monomer ratio of 1/1) are dissolved in 50 ml of dichloromethane. When the polymer is fully dissolved 45 mg of triptoreline acetate are added and then suspended by sonication.

70 g of silicone of 350 cts is added slowly with intensive stirring. And when all the silicone has been added the content of the reactor is poured onto 2.5 l of heptane and stirred for 1 hour.

The micro-capsules are recovered by filtration and dried under vacuum for 48 hours.

EXAMPLE 4: IN VITRO DETERMINATION OF THE DRUG RELEASE BY THE MICRO-CAPSULES OBTAINED

Material Needed:
 12 plastic 10-ml tubes with lid.
 1 rack for tubes.

Procedure:

Approximately 10 mg of micro-capsules containing leuprolide obtained according to example 1 are weighed into 12 10-ml tubes.

To each tube 2 ml of phosphate buffer 1/30 M and pH=7.0 are added.

Each tube is gently shaken to suspend the micro-capsules in the buffer, the tubes are sealed and placed in an oven at 37° C.

Taking samples for the control of the hydrolysis is carried out in accordance with the following table:

TABLE 1

Taking samples for analysis of leuprolide released.

| Time | Tube no. | Type of analysis |
|---|---|---|
| 1 h | 1, 2 | Supernatant |
| 3 h | 3 | Supernatant |
| 6 h | 4 | Supernatant |
| 1 d | 5 and 6 | Pellet |
| 2 d | 7 | Pellet |
| 4 d | 8 | Pellet |
| Point | | |
| 8 d | 10 | Pellet |
| 11 d | 1 and 11 | Pellet |
| 14 d | 2 | Pellet |
| 18 d | 3 and 12 | Pellet |
| 23 d | 9 | Pellet |
| 29 d | 4 and 5 | Pellet |

The analysis of leuprolide released is carried out by HPLC in the following conditions:
 COLUMN: Kromasil C-8; 25×0.45 cm
 ELUENT: Acetonitrile/water 30/70+0.05% trifluoracetic acid
 FLOW RATE: 1 ml/min
 DETECTION: UV 280 nm.

The samples are taken at the times indicated in table 1 and the analysis carried out by quantifying the peptide released in the supernatant (supernatant analysis) or the residual peptide inside the micro-capsule (pellet analysis) depending on the hydrolysis time, as indicated in table 1.

The result of this analysis is indicated in FIG. 1. In this FIGURE, the results obtained are compared with a control assay performed with leuprolide microcapsules in which triethyl citrate has not been incorporated, in accordance with the method of Example 1.

The invention claimed is:

1. A method for delivering a peptide analog of luteinizing hormone releasing, hormone (LHRH) selected from the group consisting of triptorelin, leuprolide, goserelin, buserelin and cetrorelix at a modulated rate to a subject in need thereof, said method comprising: administering to the subject an amount of microcapsules of a polymer selected from a polylactic acid polymer or a lactic-co-glycolic copolymer containing the peptide analog to provide a therapeutic effect, wherein the polymer incorporates triethyl citrate as an additive, wherein the triethyl citrate is added in a range of between 2.7% and 4.4% by total weight of the microcapsule components, and wherein the triethyl citrate produces a modulation of the release of the peptide analog from the microcapsules and a reduction of the initial release rate of the peptide analog from the microcapsules as compared to an identical microcapsule in the absence of triethyl citrate.

2. The method according to claim 1, wherein the polymer is a lactic-co-glycolic copolymer comprising lactate and glycolate units which are present in a ratio of between 99:1 and 10:90, both inclusive.

3. A method for delivering a peptide analog of luteinizing hormone releasing hormone (LHRH) selected from the group consisting of triptorelin, leuprolide, goserelin, buserelin and cetrorelix at a modulated rate to a subject to whom a plurality of microcapsules containing said peptide analog are administered, said method comprising:
(a) forming a plurality of microcapsules containing the peptide analog by
 (i) dissolving a polymer selected from a polylactic acid polymer or a lactic co-glycolic copolymer and triethyl citrate in a solvent in which said polymer and said triethyl citrate are soluble to form a solution;
 (ii) adding the peptide analog to the solution to form a peptide suspension in said solution;
 (iii) adding an alkyl derivative to the solution to produce deposition of the polymer and the triethyl citrate on the peptide analog;
 (iv) adding the suspension obtained in step (ii) to a solution in which said polymer and triethyl citrate are not soluble to harden and precipitate microcapsules thus formed; and
 (v) isolating the microcapsules thus formed,
wherein the polymer incorporates triethyl citrate as an additive, wherein the triethyl citrate is added in a range of between 2.7% and 4.4% by total weight of the microcapsule components, and
(b) administering a sufficient amount of said microcapsules containing the peptide analog to provide a therapeutic effect to said subject, wherein the triethyl citrate produces a modulation of the release of the peptide analog from the microcapsules and a reduction of the initial release rate of the peptide analog from the microcapsules as compared to an identical microcapsule in the absence of triethyl citrate.

4. The method according to claim 3, wherein a ratio between lactate and glycolate units in the lactic co-glycolic copolymer is between 99:1 and 10:90, both inclusive.

5. The method according to claim 3, wherein the alkyl derivative is silicon oil.

6. The method according to claim 1, wherein the lactic-co-glycolic copolymer comprises lactate and glycolate units present in a ratio of 1:1.

7. The method according to claim 1, wherein the molecular weight of the lactic-co-glycolic polymer is 50,000.

8. The method according to claim 1, wherein the peptide analog of LHRH is leuprolide.

9. The method according to claim 1, wherein the peptide analog of LHRH is leuprolide acetate.

10. A microcapsule comprising:
 i. a peptide analog selected from leuprolide, octreotide or triptorelin;
 ii. a polymer selected from a polylactic acid polymer or a lactic-co-glycolic copolymer containing the peptide analog; and
 iii. triethyl citrate;
 wherein the polymer incorporates triethyl citrate as an additive, wherein the triethyl citrate is added in a range of between 2.7% and 4.4% by total weight of the microcapsule components and wherein the triethyl citrate produces a modulation of the release of the peptide analog from the microcapsules and a reduction of the initial release rate of the peptide analog from the microcapsules as compared to an identical microcapsule in the absence of triethyl citrate.

* * * * *